United States Patent [19]

Welch et al.

[11] Patent Number: 4,922,903
[45] Date of Patent: May 8, 1990

[54] HANDLE FOR ELECTRO-SURGICAL BLADE

[75] Inventors: Daniel P. Welch, Zimmerman; Peter Stasz, Moundsview, both of Minn.

[73] Assignee: Everest Medical Corporation, Brooklyn Center, Minn.

[21] Appl. No.: 254,248

[22] Filed: Oct. 6, 1988

[51] Int. Cl.⁵ .............................................. A61B 17/39
[52] U.S. Cl. ........................................ 606/37; 604/22; 606/39; 606/40; 606/50; 606/45
[58] Field of Search ..................... 128/303.13, 303.14, 128/303.17, 303.19; 604/22

[56] References Cited

U.S. PATENT DOCUMENTS

| | | |
|---|---|---|
| D. 287,879 | 1/1987 | Braxton et al. . |
| 3,799,168 | 3/1974 | Peters .............................. 128/303.17 |
| 3,801,766 | 4/1974 | Morrison . |
| 3,911,241 | 10/1975 | Jarrard . |
| 4,014,343 | 3/1977 | Esty . |
| 4,021,630 | 5/1977 | Taylor . |
| 4,032,738 | 6/1977 | Esty et al. . |
| 4,034,761 | 7/1977 | Prater et al. . |
| 4,091,813 | 5/1978 | Shaw et al. .................... 128/303.14 |
| 4,112,950 | 9/1978 | Pike . |
| 4,311,145 | 1/1982 | Esty . |
| 4,398,534 | 8/1983 | Hagiwara . |
| 4,418,692 | 12/1983 | Guay .............................. 128/303.14 |
| 4,443,935 | 4/1984 | Zamba et al. . |
| 4,463,759 | 8/1984 | Garito et al. . |
| 4,492,832 | 1/1985 | Taylor . |
| 4,545,375 | 10/1985 | Cline . |
| 4,548,207 | 10/1985 | Reimels . |
| 4,593,691 | 6/1986 | Lindstrom . |
| 4,619,258 | 10/1986 | Pool . |
| 4,625,723 | 12/1986 | Altnether et al. ............... 128/303.14 |
| 4,674,498 | 6/1987 | Stasz ............................... 128/303.14 |
| 4,802,476 | 2/1989 | Noerenberg et al. .......... 128/303.14 |

Primary Examiner—Francis Jaworski
Assistant Examiner—Kennedy J. Schaetzle
Attorney, Agent, or Firm—Haugen and Nikolai

[57] ABSTRACT

An electro-surgical implement with an improved handle having a cutting mode of operation and a coagulating mode of operation. The implement includes a blade member having an electrically conductive pad area, and a predetermined pattern of electrical conductors. Electrical switch apparatus is contained in the handle member for altering the mode of operation between the cutting mode and coagulating mode when the handle member is in a locked disposition. Apparatus is also contained within the handle member for vibrating the blade member at a predetermined frequency and amplitude sufficient to create cavitation to prevent buildup of tissue and debris, and apparatus for energizing the blade for cutting and coagulating including apparatus for forcing the electrically conductive pad area against the vibration apparatus when the handle member is in a locked disposition. Mechanical switch apparatus is included to allow safe removal of the blade. An electrical cable member having a plurality of conductors therein provides electrical signals to activate the blade member.

7 Claims, 2 Drawing Sheets

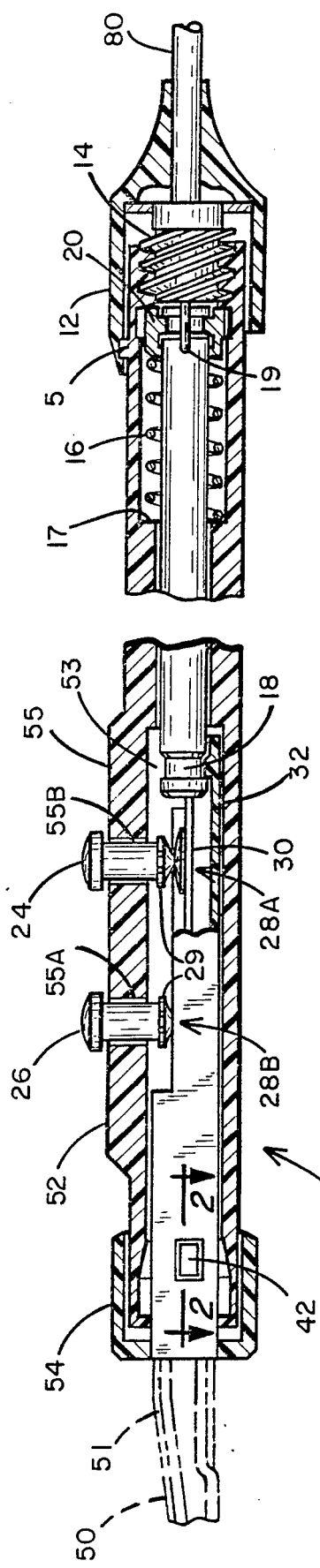
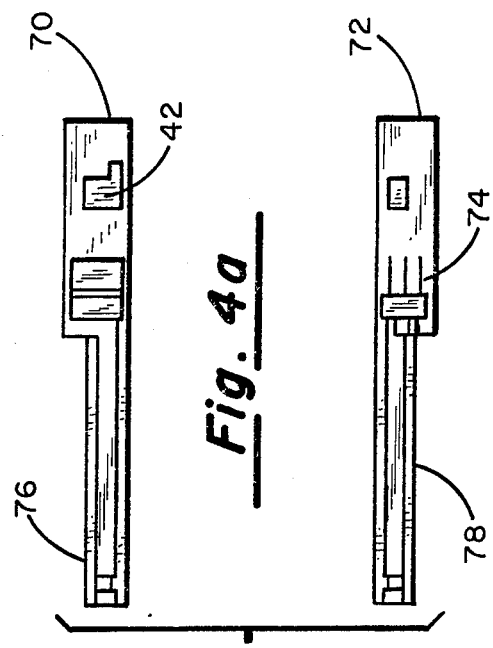
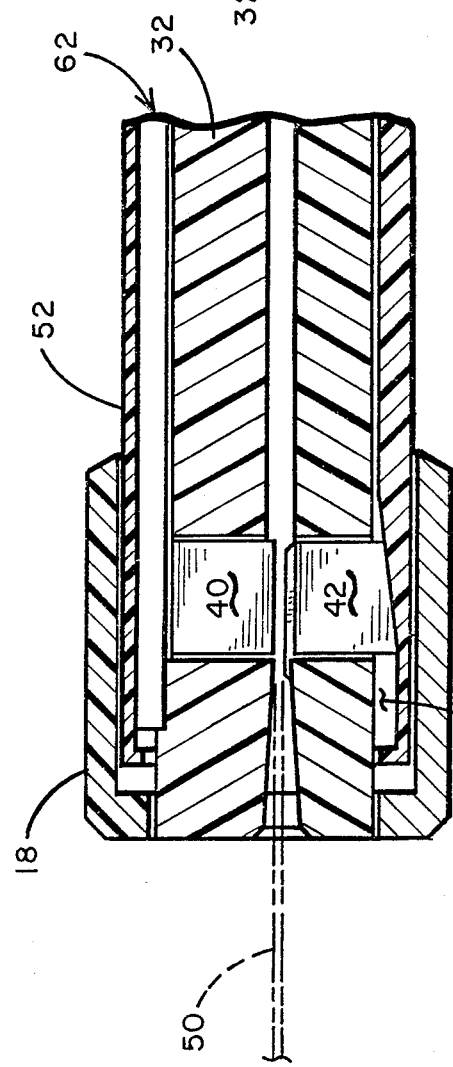

HANDLE FOR ELECTRO-SURGICAL BLADE

BACKGROUND OF THE INVENTION

I. Field of the Invention

The present invention relates to an electro-surgical instrument used for making incisions in tissue in which the blade is made to vibrate during use at a predetermined amplitude and frequency. The rapid, imperceptible movement of the blade results in cavitation at the blade's surface which frees it of the buildup of organic debris. More particularly, the present invention relates to a unique blade holder for use in connection with such a tool.

II. Discussion of the Prior Art:

As described in co-applicant's patent application Ser. No. 56,434, filed on June 1, 1987, various prior art surgical blades have been less than effective since those blades either must be made of a special material, or must carry a considerably higher voltage which may cause undue tissue damage. The teachings of patent application Ser. No. 56,434 are incorporated herein by reference. Other prior art devices do not allow for proper coupling of the blade member to the voltage source and, therefore, tend to be ineffectual. Still other prior art blade and hold assemblies have extremely elaborate and complex electrical circuits which fail to accomplish a desirable result of an effective electro-surgical tool capable of operation in more than one mode.

One of the most severe problems in the prior art is the adhesion of charred tissue and blood to the blade which uncontrollably and erratically alters the impedance between th two blade energizing conductors and, therefore, renders the instrument almost useless as a effective cutting and/or electro-cautery device. The present invention provides an electro-surgical tool which, by utilizing state-of-the-art semiconductor or printed circuit masking technology, is designed to function as an electrified blade for cutting tissue and coagulating blood. The present invention also provides surgeons with an electro-surgical tool which can be used with either a monopolar blade or a bipolar blade. The invention further provides an improved means for locking either of the foregoing type of surgical blade in place with respect to a handle and for vibrating the blade so as to produce the desired cavitation effect for cleansing the blade continuously during use. The invention still further provides safety means for deactivating both modes of operation of the blade while the blade is being replaced to prevent accidental injury for the person replacing the blade.

SUMMARY OF THE INVENTION

An electro-surgical implement having a cutting mode of operation and a coagulating mode of operation and an improved handle is disclosed. The implement includes a blade member comprising a generally flat blank, the blank having first and second opposed major surfaces and a working edge, a distal end portion, an electrically conductive pad area, and a predetermined pattern of electrical conductors extending along the working edge on the opposed major surfaces and terminating in electrical contacts on the distal end of the blank. An electrical switch means is contained in the handle member for altering the mode of operation between the cutting mode and coagulating mode when the handle member is in a locked disposition. Means is also contained within the handle member for vibrating the blade member at a predetermined frequency and amplitude sufficient to create cavitation to minimize buildup of tissue and debris, and means for energizing the blade for cutting and coagulating including means for forcing the electrically conductive pad area against the vibration means when the handle member is in a locked disposition. Mechanical switch means for altering the handle member's disposition between open and locked disposition is included wherein in open disposition the electrical switch means cannot activate either mode of operation and the blade member may be removed from the handle member. An electrical cable member having a plurality of conductors therein provides electrical signals to activate the blade member. A first portion of the electrical cable member is disposed in the hollow cavity, a second portion of the electrical cable member extends outwardly from the proximal end of the handle member and terminates in a connector, certain of the plurality of conductors in the electrical cable member being electrically coupled by the connector to the predetermined pattern of electrical conductors on the blade member, the conductive pad and the blade vibrating element.

OBJECTS

A principal object of the present invention is to provide an electro-surgical tool having an improved handle using a bipolar blade in which the two conductors are separated by an insulator, or a monopolar blade, both of which may be driven by an alternating current. Another object of the present invention is to provide an improved blade holder which incorporates a transducer element for vibrating a blade secured therein sufficiently to produce a cavitation effect, thereby minimizing adherence of tissue debris on the blade. The transducer is disposed in the handle member and in intimate contact with the blade so as to vibrate the blade, producing cavitation at the interface between the tissue and the blade.

Still another feature of the present invention is a mechanical switch means for alternating the handle member's disposition between open and locked disposition, wherein in open disposition the electrical switch means cannot activate either mode of operation and the blade member is released from the handle member so as to prevent accidental injury from persons handling the replacement blade and in locked disposition the blade member is kept in intimate contact with the transducer and is firmly held in place within the handle member.

Other objects, features and advantages of present invention will become apparent in view of the detailed specification of the preferred embodiment, drawings and claims contained herein.

DESCRIPTION OF THE DRAWINGS

The following is a brief description of the drawings wherein like numerals refer to like elements.

FIG. 1 shows the body or handle portion for the scalpel of the invention, the components shown in a cut-away view to reveal the interior design features.

FIG. 2 is a detail of the view of the proximal end of the scalpel of the invention along the line 2—2 in FIG. 1.

FIG. 4 shows the two components of the internal housing which is contained within the handle member of the invention.

DESCRIPTION OF THE PREFERRED EMBODIMENT

Figure 3:
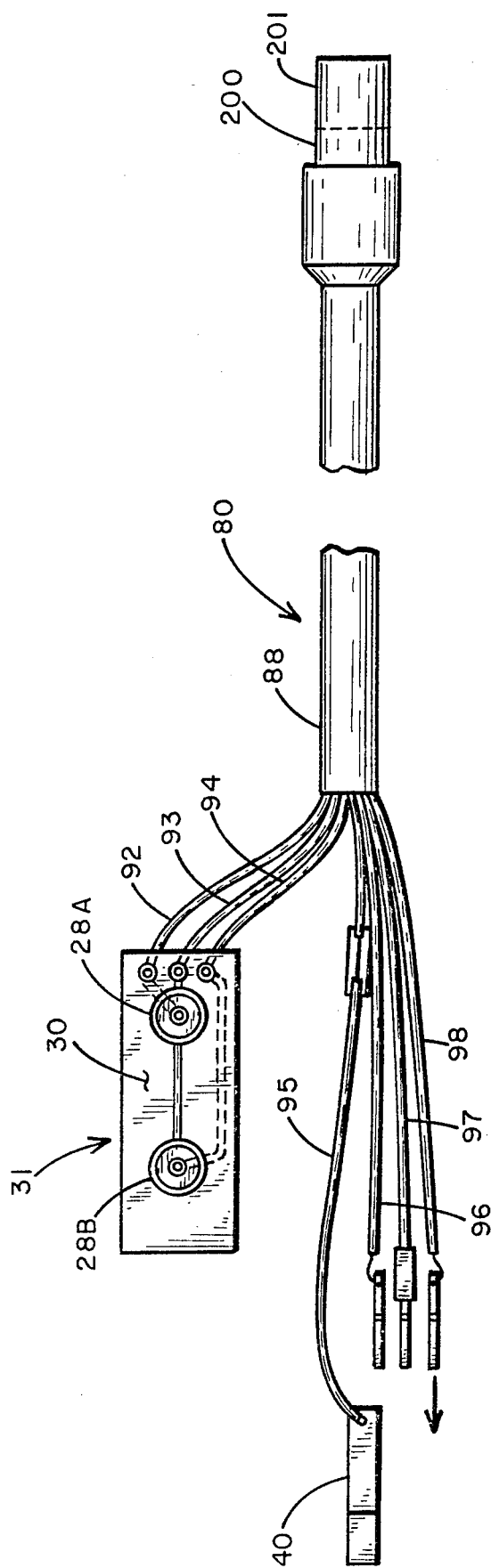
FIG. 3 shows the wiring harness of the invention, a portion of which is located within the handle body.

FIGS. 1, 2 and 4 are intended to disclose in detail the construction of the body or handle portion 10 of the electrosurgical scalpel system of the present invention. The body 10 is designed to serve as a holder for the blade and also retains the electrical assembly 31 including the diaphragm switch board 30, and the blade 50 in assembled relation when the scalpel is in use.

Figure 5:
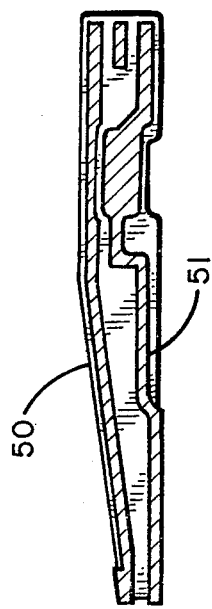
FIG. 5 shows one example of a spatula blade which may be used in the invention as a replaceable blade member.

As is best shown in FIG. 1, the scalpel body 10 is preferably molded from plastic and includes a cable bundle 80 which is described hereinbelow with reference to FIG. 3, and other elements in the invention are contained in the handle member within channel 53 as described below. The electrosurgical implement shown in FIG. 1 has a cutting mode of operation and a coagulating mode of operation. The blade member 50 comprises a generally flat blank, the blank having first and second opposed major surfaces and a working edge, a distal end portion, an electrically conductive pad area, and a predetermined pattern of electrical conductors extending along the working edge on the opposed major surfaces and terminating in electrical context on the distal end portion of the blank. Refer to FIG. 5 which shows a top view of one such spatula type of blade 50 having electrical conductor pads 51 imprinted thereon.

Still referring to FIG. 1, the housing 52 further has a mounting surface 55 having two holes 55a and 55b suitably spaced and with sufficient diameter to accept push buttons 24 and 26. In operation, push button 26 when depressed by the operator activates the cutting mode of operation of the scalpel when the handle member is in a locked disposition. Push button 24 when depressed by the operator activates the coagulation mode of operation of the scalpel when the handle member is in the locked disposition. The push buttons 24 and 26 are retained within housing 52 by means of locking C-rings 29 or other well known retaining means. Also shown is one of two diaphragm switches 28A and 28B, one of which is disposed under each of the push buttons 24 and 26 and mounted on diaphragm switch board 30.

Still referring to FIG. 1, tail sleeve 12 having integral screw member 14 is slidably mounted to housing 52 at the distal end of the handle member 10. Also shown is push rod 18, compression spring 16 and lock collar 20, all of which elements cooperate in combination with the other elements described below to provide compression in order to switch the handle member from open to locked disposition. Tail sleeve 12 has a channel for accepting cable bundle 80 as does push rod 18. Push rod 18 is kept in intimate contact with screw member 14 and compression spring 16 encompasses a portion of push rod 18. Push rod 18 may advantageously have slots adapted to accept detents 19 in lock collar 20, holding lock collar 20 in place. The channel 53 is formed to provide edge 17 such that the compression spring 16 is captured between edge 17 and lock collar 20. Channel 53 is appropriately grooved at the distal end so as to accept the screw member 14, thereby holding tail sleeve 12 in place. A small detent 5 may be provided on the exterior of housing 52 to prevent the tail sleeve from being inadvertently unscrewed, detaching it from the handle member. The proximal end of push rod 18 is attached to internal housing 32. Diaphragm switch printed circuit board 30 is mounted on internal housing 32. Internal housing 32 comprises two sections, as shown in FIG. 4 and as discussed hereinbelow. Also contained within internal housing 32 at the proximal end of the handle member 10 is a boss or wedge 42.

As best shown in FIG. 3, the electrical assembly 80 includes an insulated cable sheath 88 containing seven separately insulated wires 92-98, a switch assembly 31 comprised of a pair of diaphragms switches 28A and 28B mounted on board 30, one for the cutting mode of operation and one for the coagulating mode of operation as explained above, and a transducer 40. One end of each wire 92-98 of cable 80 is connected through a seven-pin connector 200 to an electro-surgical generator apparatus (not shown) which provides the necessary R.F. power allowing the scalpel to be operated in any one of several modes determined by the mode selection switches 28 as activated by push buttons 24 and 26, respectively, on the scalpel body. The connector 200 may include a flexible insertion section 201 comprised of a thermal plastic rubber which aids in preventing fractures or other damage to the connector upon accidental impact (e.g., if dropped). As shown in FIG. 3, wire 92 is connected to one side of diaphragm switch 28A which is used to control the coagulating function of the scalpel. Wire 94 is similarly connected to one side of diaphragm switch 28B which is used to control the cutting function of the scalpel. A common wire 93 is connected to the other side of both switches 28A and 28B. Wire 95 is connected at one end to supply energy to the transducer 40. Wires 96-98 are connected in a manner suitable to energize blade 50. Wires 96, 97 and 98 are retained in individual contact slots (shown in FIG. 4) which are molded into the internal housing 32.

As shown in FIG. 4, internal housing 32 is comprised of two sections, a first side portion 70 and a second side portion 72. Each side portion has a groove shown as 76 and 78 for accepting the diaphragm printed circuit board 30 when the internal housing is assembled. The second side portion also has contact slots 74 suitable for accepting and retaining one end of wires 96, 97 and 98 in a relationship so as to contact electrical conductors on blade 50 when blade 50 is plugged into handle member 10 and handle member 10 is in the locked disposition.

Referring now to FIG. 2 which shows a detail along line 2—2 of FIG. 1, note that the channel 53 flares out at the proximal end of housing 52. Transducer 40 is also mounted in one portion of internal housing 32 in intimate contact with heat sink and transducer reaction plate 62 such that when transducer 40 is activated by means of an electrical signal transmitted by electrical conductor 95 heat sink and transducer reaction plate 62 imparts vibration to the replaceable blade 50 instead of the external housing. In operation, when the tail sleeve 12 is screwed into the handle member, the compression spring 16 is compressed and push rod 18 is pushed toward the proximal end forcing internal housing 32 in the same direction. This action results in the boss 42 being pushed forward into the wider part of the flared end in the proximal end of channel 53 thereby releasing the blade 50 from contact with the transducer 40 and at the same time moving the diaphragm switches 28A and 28B out from under the cutting and coagulating switches 24 and 26. Since the diaphragm switches are pushed forward and away from the push buttons 24 and 26, an accidental pushing of either button will not activate the blade thereby preventing injury to a person removing or replacing a blade.

In the opposite disposition when tail splash ring 14 is unscrewed sufficiently to release compression spring 16, compression spring 16 being stiff enough to provide compression between the transducer and the blade, the push rod, which is also attached to internal housing 32, is withdrawn towards the distal end of the handle member bringing the cutting and coagulating switches back into alignment with the push buttons and forcing. At the same time, the boss or wedge 42 is forced up against the blade 50 putting the blade 50 in intimate contact with transducer 40. In this second or locked handle disposition, the blade is ready for activation and use. Finally, a front sleeve 54 is attached to the housing on the proximal end of the scalpel handle member 10 for ease in cleaning debris off of the scalpel.

Referring now to FIG. 5, one example of a spatula blade 50 having conductor pads 51 is shown. Such a blade may be advantageously used with the present invention. One illustrative embodiment of such an electrosurgical blade is described as a silicon nitride electrosurgical blade in co-applicant's copending application submitted in Aug. 1988 and entitled "Silicon Nitride Electrosurgical Blade", the teachings of which are incorporated herein by reference for background material.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and have various modifications, both as to equipment details and operating procedures without departing from the scope of the invention itself.

What is claimed is:

1. An electro-surgical implement having a cutting mode of operation and a coagulating mode of operation comprising:
    (a) a blade member comprising a generally flat blank, the blank having first and second opposed major surfaces and a working edge, a distal end portion, an electrically conductive pad area, and a predetermined pattern of electrical conductors extending along the working edge on the opposed major surfaces and terminating in electrical contacts on the distal end portion of the blank;
    (b) an elongated insulating handle member having a hollow cavity therein, a proximal end and a distal end and means for retaining the blade member, in either an open or a locked disposition;
    (c) electrical switch means contained in the handle member for altering the mode of operation between the cutting mode and coagulating mode when the handle member is in a locked disposition;
    (d) means contained within the handle member for vibrating the blade member at a predetermined frequency and amplitude sufficient to create cavitation to prevent buildup of tissue and debris, and means for energizing the blade for cutting and coagulating, the handle means including means for forcing the electrically conductive pad area against the vibration means when the handle member is in locked disposition;
    (e) mechanical switch means for altering the handle member's disposition between open and locked disposition such that in open disposition the electrical switch means cannot activate either mode of operation and the blade member is released from the handle member; and
    (f) an electrical cable member having a plurality of conductors therein, a first portion of the electrical cable member being disposed in the hollow cavity, a second portion of the electrical cable member extending outwardly from the proximal end of the handle member and terminating in a connector, certain of the plurality of conductors in the electrical cable member being electrically connected to the predetermined pattern of electrical conductors on the blade member, the conductive pad and the blade vibrating element.

2. The apparatus of claim 1 wherein the electrical switch means comprises:
    (a) coagulating and cutting operational mode push buttons slidably contained within the handle member;
    (b) a printed circuit board contained within the handle member; and
    (c) diaphragm switches corresponding to the coagulating and cutting operational mode push buttons each diaphragm switch disposed to be activated by the corresponding push button when the handle member is in the locked disposition.

3. The apparatus of claim 2 wherein the mechanical switch means comprises:
    (a) a tail sleeve including a screw member integral thereto where the tail sleeve slidably engages the handle member and is capable of being twisted into first and second positions where the first position forces the handle member into the open disposition and the second position forces the handle member into the locked disposition;
    (b) a push rod contained within the handle member having a distal end and a proximal end wherein the distal end is in intimate contact with one end of the screw member;
    (c) a compression spring which encompasses the push rod;
    (d) a lock collar which is attached to the push rod and which captivates the compression spring at one end;
    (e) a retaining member integral with the handle member which captivates the compression spring at the other end of the spring; and
    (f) a slidable internal housing upon which the cutting and coagulating diaphragm switches printed circuit board is mounted and including a wedging member which disengages the blade member and disables the electrical switch means when the handle member is in the open disposition.

4. An improved handle for use in an electro-surgical implement having a cutting mode of operation and a coagulating mode of operation and adapted to accept a blade member comprising a generally flat blank, the blank having first and second opposed major surfaces and a working edge, a distal end portion, an electrically conductive pad area, and a predetermined pattern of electrical conductors extending along the working edge on the opposed major surfaces and terminating in electrical contacts on the distal end portion of the blank comprising:

(a) an elongated insulating handle member having a hollow cavity therein, a proximal end and a distal end and means for retaining the blade member, in either an open or a locked disposition;

(b) electrical switch means contained in the handle member for altering the mode of operation between the cutting mode and coagulating mode when the handle member is in the locked disposition;

(c) means contained within the handle member for vibrating the blade member at a predetermined frequency and amplitude sufficient to create cavitation to minimize buildup of tissue and debris, and means for energizing the blade for cutting and coagulating, the handle means including means for forcing the electrically conductive pad area against the vibration means when the handle member is in locked disposition;

(d) mechanical switch means for altering the handle member's disposition between open and locked disposition such that in open disposition the electrical switch means cannot activate either mode of operation and the blade member is released from the handle member; and (e) an electrical cable member having a plurality of conductors therein, a first portion of the electrical cable member being disposed in the hollow cavity, a second portion of the electrical cable member extending outwardly from the proximal end of the handle member and terminating in a connector, certain of the plurality of conductors in the electrical cable, member being electrically connected to the predetermined pattern of electrical conductors on the blade member, the conductive pad and the blade vibrating element.

5. The apparatus of claim 4 wherein the electrical switch means comprises:

(a) coagulating and cutting operational mode push buttons slidably contained within the handle member;

(b) a printed circuit board contained within the handle member; and (c) diaphragm switches corresponding to the coagulating and cutting operational mode push buttons each diaphragm switch disposed to be activated by the corresponding push button when the handle member is in the locked disposition.

6. The apparatus of claim 5 wherein the mechanical switch means comprises:

a tail sleeve including a screw member integral thereto where the tail sleeve slidably engages the handle member and is capable of being twisted into first and second positions where the first position forces the handle member into the open disposition and the second position forces the handle member into the locked disposition;

(b) a push rod contained within the handle member having a distal end and a proximal end wherein the distal end is in intimate contact with one end of the screw member;

(c) a compression spring which encompasses the push rod;

(d) a lock collar which is attached to the push rod and which captivates the compression spring at one end;

(e) a retaining member integral with the handle member which captivates the compression spring at the other end of the spring; and (f) a slidable internal housing upon which the cutting and coagulating diaphragm switches printed circuit board is mounted and including a wedging member which disengages the blade member and disables the electrical switch means when the handle member is in the open disposition.

7. The apparatus of claim 1 wherein the connector further includes a flexible insertion section.

* * * * *